(12) United States Patent
Gafni et al.

(10) Patent No.: US 8,083,786 B2
(45) Date of Patent: Dec. 27, 2011

(54) THERMAL STIMULATION PROBE AND METHOD

(75) Inventors: Ehud Gafni, Ramat Yishai (IL); Yelena Granovsky, Haifa (IL)

(73) Assignee: Medoc Ltd., Ramat-Yishai (IL)

( * ) Notice: Subject to any disclaimer, the term of this patent is extended or adjusted under 35 U.S.C. 154(b) by 1452 days.

(21) Appl. No.: 10/558,077

(22) PCT Filed: May 20, 2004

(86) PCT No.: PCT/IL2004/000435
§ 371 (c)(1),
(2), (4) Date: Sep. 5, 2006

(87) PCT Pub. No.: WO2004/103230
PCT Pub. Date: Dec. 2, 2004

(65) Prior Publication Data
US 2007/0010860 A1    Jan. 11, 2007

Related U.S. Application Data

(60) Provisional application No. 60/472,480, filed on May 22, 2003.

(51) Int. Cl.
*A61F 7/00* (2006.01)

(52) U.S. Cl. .................. 607/96; 606/20; 606/27

(58) Field of Classification Search ............ 606/20, 606/27; 607/96
See application file for complete search history.

(56) References Cited

U.S. PATENT DOCUMENTS

| | | | |
|---|---|---|---|
| 3,971,229 A | 7/1976 | Privas | |
| 4,582,057 A * | 4/1986 | Auth et al. | 606/31 |
| 5,242,437 A * | 9/1993 | Everett et al. | 606/15 |
| 6,567,696 B2 * | 5/2003 | Voznesensky et al. | 607/3 |
| 6,741,895 B1 * | 5/2004 | Gafni et al. | 607/138 |
| 2002/0107543 A1 | 8/2002 | Voznesensky et al. | |

FOREIGN PATENT DOCUMENTS

| | | |
|---|---|---|
| EP | 0073865 | 3/1983 |
| EP | 0089806 | 9/1983 |
| EP | 0840078 | 5/1998 |
| WO | WO 85/00226 | 1/1985 |

* cited by examiner

*Primary Examiner* — Roy Gibson
*Assistant Examiner* — Kaitylyn Smith (57) ABSTRACT

A physiological thermal stimulation probe, comprising: (a) an electrically controlled heat control element with a relatively low thermal capacity and adapted for contact with tissue on one side thereof; (b) a thermal sink/source with a relatively high effective thermal capacity and a relatively low thermal impedance, such that said thermal sink/source sink can rapidly change a temperature of said heat control element, at a rate above 10 degrees Celsius per second, from a temperature of below 100 degrees Celsius; and (c) circuitry which activates said heat control element to achieve a desired temperature stimulation profile of said tissue.

9 Claims, 7 Drawing Sheets

THERMAL STIMULATION PROBE AND METHOD

RELATED APPLICATIONS

The present application is a US National Phase of PCT Application No. PCT/IL2004/000435, filed on May 20, 2004, published as WO 2004/103230. The present application also claims the benefit under 119(e) of U.S. provisional patent application No. 60/472,480, the disclosure of which is incorporated herein by reference.

FIELD OF THE INVENTION

The present invention is related to thermal stimulation of tissue.

BACKGROUND OF TH INVENTION

The pain mediating system in a human consists of two kinds afferent fibers: A-delta and C-fibers. These afferent pain fibers characterized by different physiological parameters, for example, conduction velocity (15-50 ml/s for A-delta fibers and <2 m/s for C-fibers). These two fiber types project to different parts of the dorsal horn of the spinal cord. In addition, stimulation of each kind of nociceptors evokes different type of sensation: A-delta fibers mediate first (sharp, pin-prick) pain sensation; C-fibers mediate the sensation of second pain usually perceived as burning sensation.

Dysfunction of pain- and sensory-mediated systems often accompanies various neurological disorders as well as other pain syndromes of unknown etiology. Therefore, selective activation and identification of the response may offer very significant opportunity for proper diagnostic and treatment in pain patients. The most popular tool for the evaluation of A-delta functioning is radiant heat laser stimuli that evoke pin-prick sensation (e.g., user response) and well defined potential on EEG recording. However, selective activating with subsequent recording for the evaluation of C-fibers activity is apparently more difficult. Some existed methods for the selective C-fibers activation are based on laser stimulation following the ischemic block of A-delta fibers; applying laser stimuli on very tiny cutaneus surface areas (d=0.5 mm) using special lens; or by stimulating skin surface through special filter. These methods, however, have not found widespread clinical use, possibly due to their complexity and/or poor sensation generation quality.

Peltier elements have been used for heat and/or cold stimulating a body portion for evaluating nervous sensitivity, for example, as described in WO 00/23030, the disclosure of which is incorporated herein by reference.

An article in Pain 100 (2002) 281-290, the disclosure of which is incorporated herein by reference, describes a cold-stimulation device.

During brain surgery there is a general difficulty of determining if tissue about to be damaged serves a crucial brain function.

In surgical procedures, patients are typically given a mixture of drugs to have the following three effects: anesthesia (loss of consciousness), pain reduction and immobilization. Due to the difficult in determining if the correct effect has been achieved, there exists a problem of patients which are immobilized but are conscious and/or feel pain during surgery. Even if not conscious, pain can cause an increase in sensed or even chronic pain after surgery,

SUMMARY OF THE INVENTION

An aspect of some embodiments of the invention relates to a physiological temperature stimulation probe with a fast cooling and heating ability. In an exemplary embodiment of the invention, the probe includes a controllable temperature profile including at least one, and optionally two or more of an onset rate, a plateau temperature, duration, change rate and a decay rate. In an exemplary embodiment of the invention, the probe is controllable to produce various stimulation sequences, including, for example oscillations or non-uniform pulse trains.

An aspect of some embodiments of the invention relates to a physiological temperature stimulation probe structure including a primed heat-sink or source in close thermal contact with a temperature stimulation element such that the readied heat sink/source can rapidly change the temperature of the temperature stimulation element. In an exemplary embodiment of the invention, the temperature stimulation element is actively controlled and optionally continuously controlled to offset the effect of the sink/source when not desired. Alternatively or additionally, one or more temperature sensors are used to provide closed loop control of the stimulation element temperature. In an exemplary embodiment of the invention, the heat sink/source has a low enough thermal impedance so that it can quickly change the temperature of the temperature stimulation element and also a high enough thermal capacity to provide such an effect.

In an exemplary embodiment of the invention, an electrically controllable temperature stimulation element is used.

In an exemplary embodiment of the invention, the following structure is used. The stimulation element is a thin heating foil heated by resistance. One or more temperature sensors are optionally provided to determine its actual temperature. Alternatively, for example, the temperature may be estimated from its resistance. In thermal contact with the heating foil is a metal plate (or other material with high heat conductivity (low thermal impedance), such as diamond), which serves as a heat sink/source. Optionally, the sink/source has a thermal mass considerably greater than that of the foil. On the side of the plate opposite the heating foil is optionally provided a heating and/or cooling element, such as a heat pump coil, a Peltier element or a bath of temperature controlled water. One or more temperature sensors are optionally provided to determine the temperature of the plate, for example, one or the other of the sides or its middle. Optionally, the heating and/or cooling element are used to maintain a desired temperature of the plate, possibly with a lower response time than the frequencies of changes of the stimulation temperature. It should be noted that, in an exemplary embodiment of the invention, a temperature gradient is maintained in the plate by the opposite effects of the Peltier element and the heating foil. If, for example, the plate is cooled, turning off the heating of the foil will drop its temperature down towards the cold temperature of the plate. Increasing the heating of the foil will rapidly raise its temperature. In an exemplary embodiment of the invention, the heating and cooling rate are at or greater than 5, 10, 20, 30, 50 or 70 degrees Celsius per second. Optionally, a liquid heat sink, such as a water heat exchanger having externally cooled water, is provided for the Peltier element.

An aspect of some embodiments of the invention relates to methods of stimulation using rapid heating and cooling physiological temperature stimulation probes. In an exemplary embodiment of the invention, the stimulation is applied at a rate (e.g., >0.33 Hz or 2 or 3 Hz) fast enough to evoke a windup phenomena which selectively activates C-fiber without using additional, chemical, treatments. Alternatively or additionally, the temperature control may be used to selectively activate various A-delta fibers, for example, low threshold and high threshold. Alternatively or additionally, cold-sensing fibers may be selectively stimulated using pulses of low temperature. It should be noted that, in an exemplary embodiment of the invention, relatively large areas or small areas can be selectively stimulated.

An aspect of some embodiments of the invention relates to brain function mapping during brain surgery. In operating on the brain, delicate brain structures, are often damaged. In an exemplary embodiment of the invention, a CHEP (contact heat evoked potential) device is sued for identifying pain sensing regions of the brain. In one example, a surgeon holds recording electrodes (or as part of a glove or probe) and measures the evoked response to a heat or cold stimulation, the electrode scan be moved so that a most strongly responding or least strongly responding brain region is identified. Optionally, different brain centers are identified using different stimuli, for example using one or more of noxious cold, noxious heat, innocuous cold, innocuous heat, vibration and electrical stimulation of nerves.

An aspect of some embodiments of the invention relates to monitoring during surgery, for example monitoring of quality of pain blocking, depth of analgesia and/or depth of anesthesia. In an exemplary embodiment of the invention, CHEP is used to detect an evoked potential and indicate the degree of pain blocking. For example, perfect pain blocking may prevent any evoked potential from being detected. Alternatively or additionally, CHEP and/or a non-pain stimuli, such as vibration is used to detect an evoked potential signal indicating a level of consciousness. Optionally, the thresholds and/or amplitudes used are calibration for a group of patients or for the particular patient.

There is thus provided in accordance with an exemplary embodiment of the invention, a physiological thermal stimulation probe, comprising:

(a) an electrically controlled heat control element with a relatively low thermal capacity and adapted for contact with tissue on one side thereof;

(b) a thermal sink/source with a relatively high effective thermal capacity and a relatively low thermal impedance, such that said thermal sink/source sink can rapidly change a temperature of said heat control element, at a rate above 10 degrees Celsius per second, from a temperature of below 100 degrees Celsius; and (c) circuitry which activates said heat control element to achieve a desired temperature stimulation profile of said tissue.

In an exemplary embodiment of the invention, said heat control element functions as a heating element and wherein said thermal sink/source functions as a heat sink.

In an exemplary embodiment of the invention, said heat control element functions as a cooling element and wherein said thermal sink/source functions as a heat source.

In an exemplary embodiment of the invention, said heat sink comprises a cold thermal mass. Optionally, said cold thermal mass comprises a thermally conducting plate.

In an exemplary embodiment of the invention, said heat sink comprises an active cooling element.

In an exemplary embodiment of the invention, said heat sink comprises an active cooling thermally coupled to said thermal mass.

In an exemplary embodiment of the invention, cooling element comprises a Peltier element. Alternatively or additionally, said cooling element comprises a heat pump.

In an exemplary embodiment of the invention, the probe comprises at least one temperature sensor in association with said thermal mass, wherein said circuitry applies closed loop feedback on a temperature of said thermal mass cooling element using said temperature sensor to control an activation of said active cooling element.

In an exemplary embodiment of the invention, the probe comprises at least one temperature sensor in association with said heating element, wherein said circuitry applies closed loop feedback on a temperature of said heating element using said temperature sensor to control an activation of said heating element.

In an exemplary embodiment of the invention, said circuitry samples said at least one temperature sensor at faster than 10 Hz.

In an exemplary embodiment of the invention, said circuitry samples said at least one temperature sensor at faster than 50 Hz.

In an exemplary embodiment of the invention, said circuitry controls said probe to provide a pulse of heat.

In an exemplary embodiment of the invention, said circuitry controls said probe to provide a pulse of cold.

In an exemplary embodiment of the invention, said circuitry controls said probe to selectively stimulate A-delta fibers.

In an exemplary embodiment of the invention, said circuitry controls said probe to selectively stimulate a subgroup of A-delta fibers. Optionally, said sub-group comprises cold sensing fibers. Alternatively or additionally, said sub-group comprises either high or low threshold fibers.

In an exemplary embodiment of the invention, said circuitry controls said probe to selectively stimulate C fibers.

In an exemplary embodiment of the invention, said circuitry controls said probe to generate a windup effect.

In an exemplary embodiment of the invention, said circuitry controls said probe to provide a second pain effect.

In an exemplary embodiment of the invention, said circuitry controls said probe to have a temperate raise rate of over 30 degrees Celsius per second.

In an exemplary embodiment of the invention, said circuitry controls said probe to have a temperate decrease rate of over 30 degrees Celsius per second.

In an exemplary embodiment of the invention, said heating element comprises an array of individually controllable heating elements.

In an exemplary embodiment of the invention, said heating element comprises a foil heater.

In an exemplary embodiment of the invention, said circuitry includes a trigger input for triggering stimulation.

In an exemplary embodiment of the invention, said circuitry includes a trigger output for generating an external trigger.

In an exemplary embodiment of the invention, said circuitry maintains said probe at a neutral temperature by providing an activation of said heating element to offset the effect of said heat sink.

In an exemplary embodiment of the invention, said circuitry pre-cools said heat sink.

In an exemplary embodiment of the invention, said probe comprises means for sensing brain activity.

In an exemplary embodiment of the invention, said probe comprises circuitry adapted to display a degree of pain blocking.

In an exemplary embodiment of the invention, said probe comprises circuitry adapted to display a consciousness level.

There is also provided in accordance with an exemplary embodiment of the invention, a method of stimulating tissue using a heat probe, comprising:

providing a heat sink/source at a temperature different from a neutral temperature relative to a tissue to be stimulated;

contacting said tissue with a heat control element, which heat control element is in thermal contact with said sink/source; and controlling said stimulation by selectively varying a power of said heat control element to generate at least one of a heat pulse and a cold pulse. Optionally, said heat sink/source comprises a heat sink. Alternatively or additionally, said heat control element comprises a heater.

There is also provide din accordance with an exemplary embodiment of the invention, method of controlling the application temperature of a probe, comprising:

providing a relatively large thermal mass at a first temperature;

providing a relative small thermal mass at a second temperature, which second thermal mass includes an active electrically controlled temperature control element and which relatively small thermal mass is in thermal contact with said large thermal mass; and controlling the application temperature by controlling the active element in a manner which generates an application temperature of said small thermal mass other than said first temperature. Optionally, the method comprises stopping active element to produce a sharp change in temperature of said small thermal mass. Alternatively or additionally, the method comprises powering said active element to produce a sharp change in temperature of said small thermal mass.

In an exemplary embodiment of the invention, said first and second temperatures are different.

In an exemplary embodiment of the invention, said thermal masses have a ratio of over 1:50. Optionally, said thermal masses have a ratio of over 1:100. Optionally, said thermal masses have a ratio of over 1:1000.

BRIEF DESCRIPTION OF THE FIGURES

Particular non-limiting embodiments of the invention will be described with reference to the following description of embodiments in conjunction with the figures, in which.

DETAILED DESCRIPTION OF EXEMPLARY EMBODIMENTS

Figure 1:
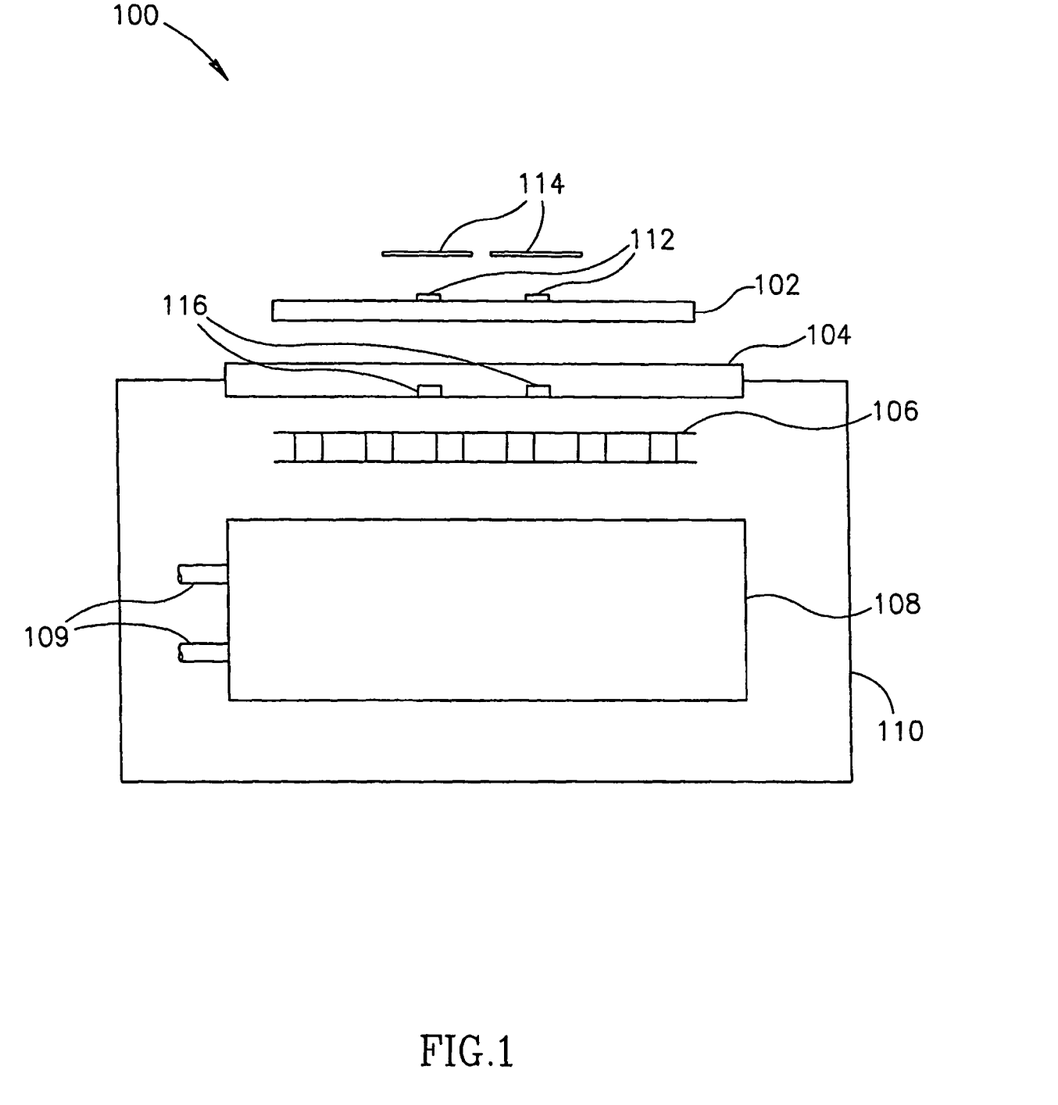
FIG. 1 is a schematic side illustration of physiological temperature stimulation probe in accordance with an exemplary embodiment of the invention.

FIG. 1 is a schematic side illustration of physiological temperature stimulation probe 100 in accordance with an exemplary embodiment of the invention. The probe comprises a contact a heating element, which is in contact with the tissue to be stimulated. In an exemplary embodiment of the invention, the heating element is a resistive foil 102, for example, a foil of Nickel-Iron optionally covered by 25 or 50 microns of Kapton on all sides (or only in contact with the skin) and having an area of 24×24 mm. Optionally, the foil heater is controllable as a linear or two dimensional array of heating elements. In an exemplary embodiment of the invention, this heating foil is used to provide a rapid onset of heating stimulation. Optionally, one or more temperature sensors 112 are provided between the foil and the tissue, optionally shielded from the tissue, for example by a thin layer of Kapton 114. These sensors are optionally used to detect and act as sensors for control of the temperature of the foil to ensure a correct stimulation. The spacing in the figure is shown for clarity and should not be construed as limiting. Exemplary probe dimensions (e.g., contact area) are 10×10 mm, 1×1 mm, 5×5 mm, 30×30 mm and intermediate, smaller or greater sizes. The probe (and optionally the thermal capacity element described below) as a whole may be elongate, for example having a cross-section matching that of the contact area.

In an exemplary embodiment of the invention, a thermal capacity element (mass) 104 is provided in thermal contact with foil 102. A temperature control element, for example a Peltier element 106, is provided in thermal contact with (or embedded in) thermal capacity element 104, and allows controlling the temperature in at least part of the mass. Optionally, one or more temperature sensors 116 are embedded in element 104, to provide feedback for such control. A potential advantage of using a Peltier element is that it allows better control (e.g., by heating and/or cooling) of the temperature of mass 104. Sensors 116 may be used to assess the temperature in one or more layers of element 104, for example, its middle or one of the sides. Optionally, a thermal sensor is provided for sensing the temperature of the Peltier element e.g., at one or both ends thereof. Optionally, resistance (or other electrical properties of the Peltier element) is used to assess such a temperature. Optionally, a Peltier element is used in place of the foil.

In an exemplary embodiment of the invention, the thermal capacity of foil 102 is significantly smaller than that of thermal capacity element 104. As will now be described, the actual stimulation temperature is determined as an interplay of the effects of foil 102 and of thermal capacity element 104. In one operational mode, thermal capacity element 104 has a relatively low temperature. However, the stimulation temperature is determined by foil 102, which is closer to the tissue and which masks the temperature of thermal capacity element 104 from reaching the tissue. A temperature gradient may be formed (and possibly maintained) in thermal capacity element 104 (or foil 102) or in a layer (if any) between element 104 and foil 102. However, if the electrification to foil 102 is reduced, thermal capacity element 104 asserts itself and causes a reduction in the stimulation temperature. This assertion is generally assisted by the low thermal impedance of element 104, in some embodiments of the invention. While various effective stimulation temperatures can be achieved by controlling the temperature of thermal capacity element 104 and the electrification of foil 102, in an exemplary embodiment of the invention, what is desirable in some embodiments of the invention, is rapid cooling to a non-stimulation temperature or to a cold stimulation temperature, assisted by the presence of a large cold thermal mass in proximity with the tissue. The use of a heating foil allows for rapid and large temperature changes.

In an exemplary embodiment of the invention, a thermal energy sink 108 is provided for Peltier element 106, for example, a water tank 216 (FIG. 2), with inlet and outlet tubes 109. The temperature in the tank may be maintained, for example by a heat pump (not shown) and optionally external to the probe, for example at between 1 and 20 degrees Celsius. Alternatively, a fan may be provided. A housing 110 is optionally provided, from which foil 102 is optionally exposed. If a thermal heat source is used, its temperature may be, for example, 40, 50 or 60 degrees Celsius. In an exemplary embodiment of the invention, the heat source/sink used is maintained at a temperature different form a neutral temperature by more than 5, 10 or 20 degrees Celsius, to allow faster changes in temperature. Alternatively, such a source/sink may be held at a body neutral temperature, for example, between 32 and 37 degrees Celsius.

It should be noted that a separate thermal capacity element is not required for some embodiments. Instead, its function can be provided, for example, a Peltier element actively maintained at a desired temperature relative to the heating element. However, a separate thermal capacity element has two potential advantages in some probe designs. First, a lower peak power to the Peltier element may be needed, as the thermal capacity element can be maintained at a relatively low temperature and its temperature fluctuations may be relatively small, due to its high capacity. Second, the rate of heat conduction from the thermal capacity element may be higher, due, for example to better contact or lower thermal impedance. It should also be noted that in some cases some amount of thermal impedance is desirable, for example to lower the power requirements of the heating element and the cooling element. It should also be noted that control of an active element may be more difficult at higher power settings, and easier for a thermal capacity element, which due to its thermal capacity changes its temperature relatively slowly.

Figure 2:
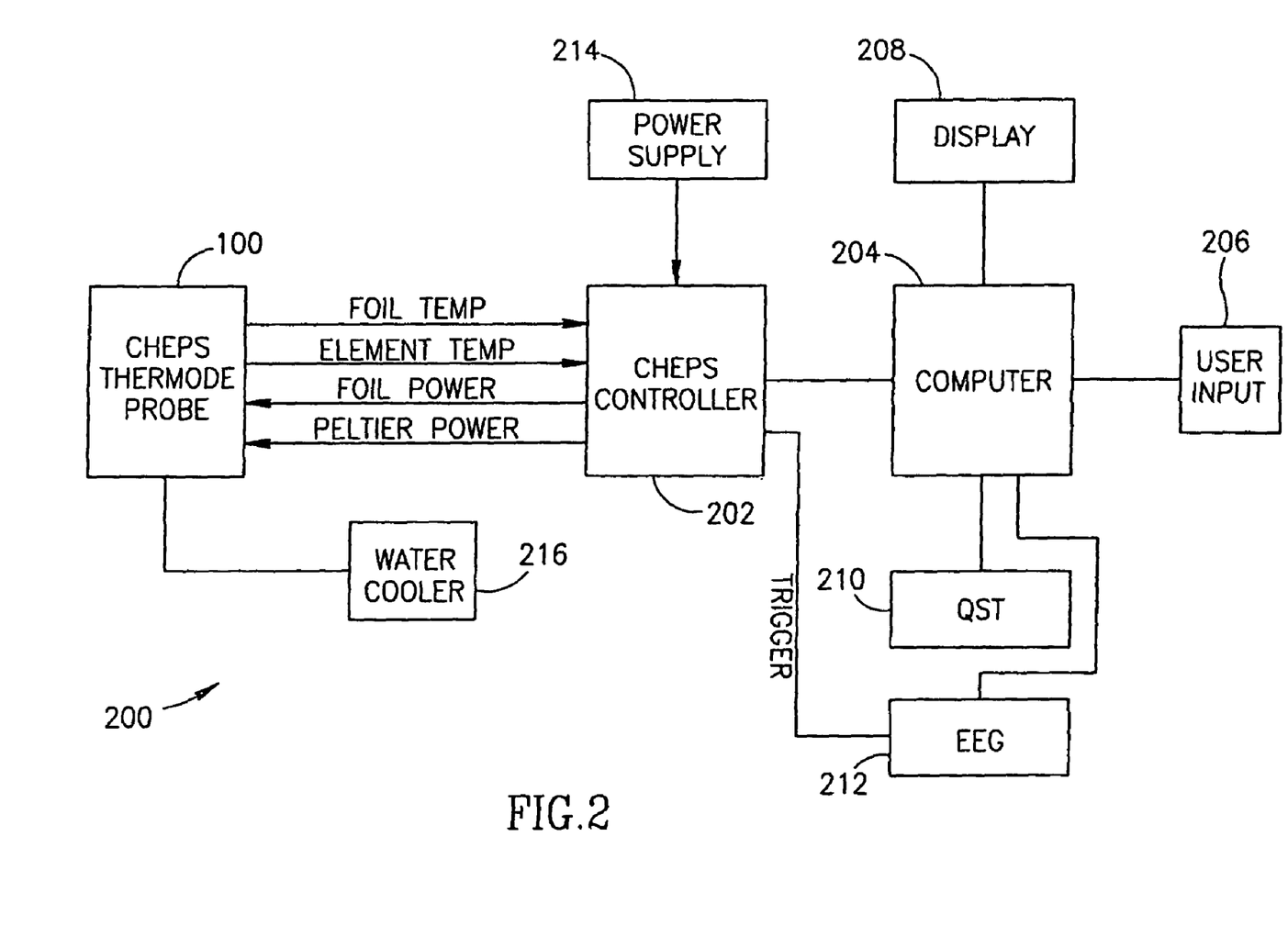
FIG. 2 is a schematic block diagram of a stimulation system including the probe of FIG. 1, in accordance with an exemplary embodiment of the invention.

FIG. 2 is a schematic block diagram of a stimulation system 200 including probe 100. It should be noted that many different configurations may be used and that of FIG. 2 is only exemplary, in particular the distribution of work between different processors and power provision between different power sources may vary.

In the configuration shown, a CHEPS (contact heat evoked potential stimulator) probe 100, as described for example in FIG. 1, is controlled by a CHEPS controller 202, optionally a dedicated controller, which receives, for example signals indicating the foil temperature and/or thermal mass temperature. Based on these signals and a desired foil temperature, controller 202 sends power signals, for example to electrify the heating foil and to activate the Peltier element. Power is optionally supplied by a power supply 214, for example gated or controlled by controller 202. In an exemplary embodiment of the invention, a computer 204 is used to manage a diagnosis session in which probe 100 is used. An optional display 208 is used to show, for example, previous and current test results and to display options to a user. A user input 206, for example a keyboard and a mouse are used to enter instructions and/or data. In an exemplary embodiment of the invention, test results are provided using user input 206 or using an EEG device 212 (optionally connected to a TTL trigger output of controller 202), to detect the evoked potential in nerves, such as in the brain. Optionally, a QST (Quantitative Sensory Testing) system 210, also available from Medoc, LTD. of Ramat Yishai, Israel, is used for electrical or other types of stimulation. The software of such a system, optionally modified, is optionally used for managing sessions and patient information, for example, for planning type of testing (staircase, alternating, random) and type of stimuli used. Optionally, electrical stimulation is provided by probe 100, for example using a plurality of electrodes that poke through or are provided on the foil heater. Alternatively, multiple sequential testing using different types of probes may be used instead.

Figure 3A:
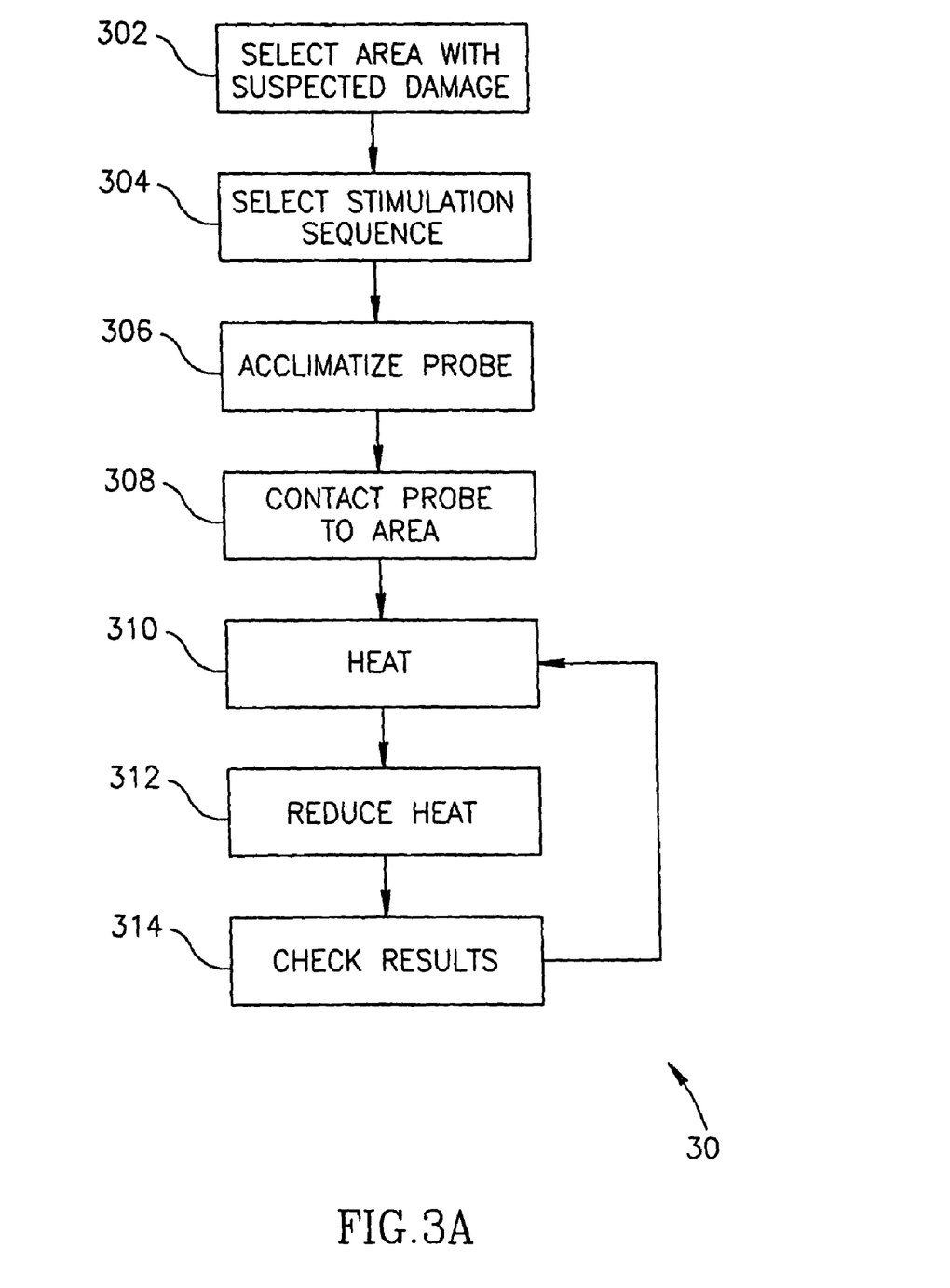
FIG. 3A is a flowchart of a method of using the system of FIG. 2, in accordance with an exemplary embodiment of the invention.

FIG. 3A is a flowchart 300 of a method of using system 200, in accordance with an exemplary embodiment of the invention. At 302, an area of a human body in which nerve damage is suspected, is selected. Different probe geometries may be used for different areas. At 304, a stimulation sequence is selected, for example a sequence to selectively stimulate A-delta or C fibers. Generally, it is desired that the probe contact the stimulated area in a manner which does not, itself, cause any stimulation. In addition, for some probe operation modes, it is required that thermal capacity element 104 be cooled for proper operation, this may take time and is illustrated by an acclimatization act 306, in which probe 100 is set up and brought to a correct temperature. It should be noted that once element 104 is cooled enough, foil 102 must be heated in order to ensure a neutral contact temperature. Alternatively, element 104 may be selectively coupled to foil 102, by a mechanical movement means (not shown). An example of neutral contact temperatures are 32 degrees Celsius for skin on extremities, 33 degrees Celsius for the face and abdomen and 37 degrees Celsius for various body orifices. Other temperatures may be used, of course.

At 308, probe 100 is contacted to the area. At 310, the probe is heated, in some cases at a high rate, for example, faster than 20, 40, 60 or 70 degrees Celsius per second, for example to a temperature such as 40, 45 or 50 degrees Celsius. At 312, the heat is reduced, possibly after a delay, which allows the cooling effect of thermal capacity element 104 to have an effect. Optionally, the effect is quite rapid, for example yielding a cooling rate of more than 10, 20, 30 or 40 degrees Celsius per second. Possibly, cooling overshoots the original neutral temperature. It should be noted that the cooling rate may be controlled by one or both of electrification level of foil 102 and temperature of element 104. In an exemplary embodiment of the invention, the target temperature of the probe can be selected, for example, at a resolution of 1, 2, 5 or 10 degrees Celsius, or a slower, intermediate or higher resolution. As described herein, the temperature of the probe can be positively controlled to reach the target temperature, possibly irrespective of environmental and/or other factors.

At 314, the results of the stimulation are assessed and a decision is made if to repeat the process. Optionally, the decision takes into account results from a QST session in which electrical stimulation is used.

It should be noted that a cold stimulation pulse can be applied by first cooling and then heating foil 102, in reverse of what is shown in FIG. 3A.

In some embodiments of the invention a passive cold thermal mass is used for cooling thermal capacity element 104 and/or foil 102, for example a chamber with dry ice or a very low temperature metal mass. Optionally, a thermocouple is provided on such a chamber to allow the effect of its exact temperature to be factored into parameter calculations.

Figure 3B:
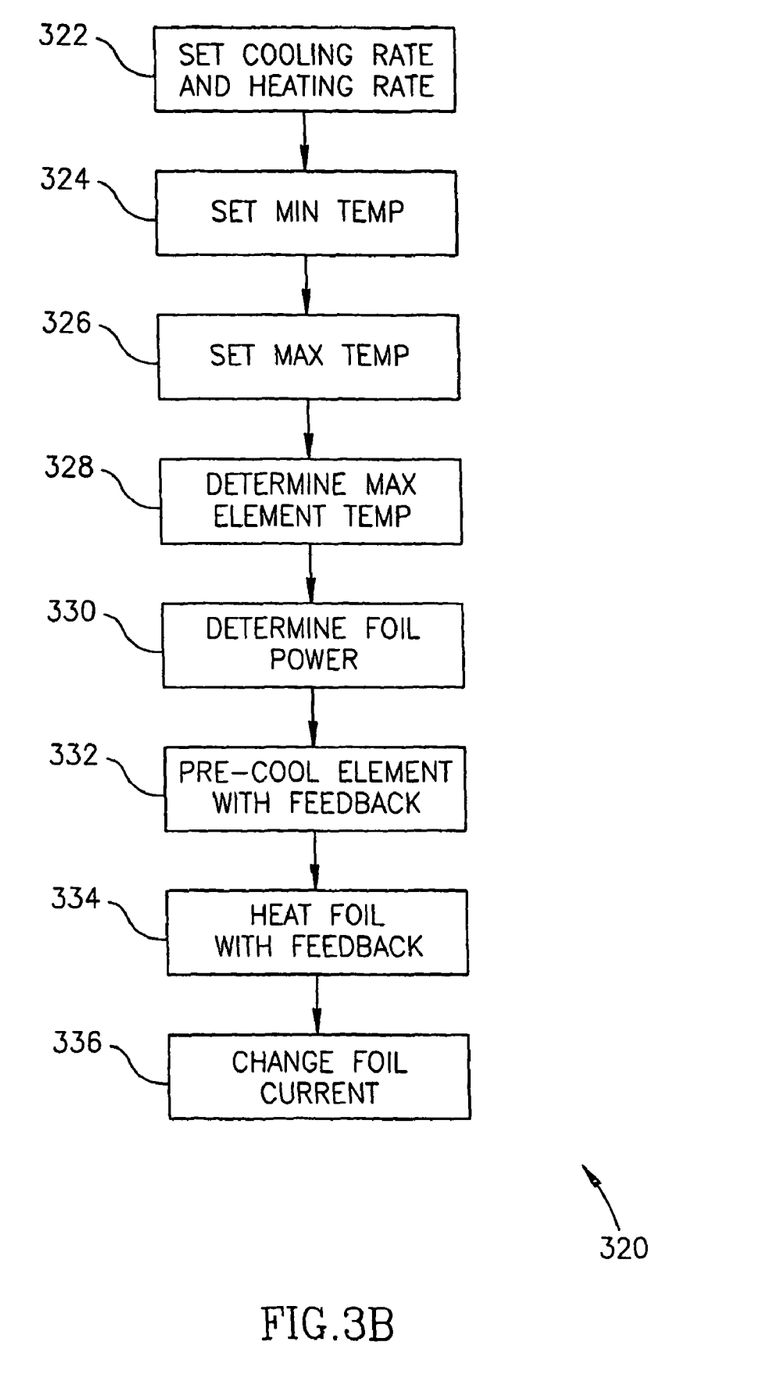
FIG. 3B is a flowchart of a method of controlling the stimulation temperature in accordance with an exemplary embodiment of the invention.

FIG. 3B is a flowchart of a method 320 of controlling the stimulation temperature in accordance with an exemplary embodiment of the invention.

In an exemplary embodiment of the invention, when applying a temperature pulse or sequence, it is assumed that mass 104 will substantially be maintained at a single temperature throughout, with temperature fluctuations being dealt with using a feedback loop using Peltier element 106 and temperature sensors 116. Desirably, Peltier element 106 is designed to be able to handle the total output (absorbed by mass 104) of foil 102 over a time period. It should be noted that during operation, the power levels supplied may change rapidly. In addition, some small temperature oscillations may be generated, depending, for example, on the rate of temperature sampling and thermal control, as compared to quality of control and prediction and thermal momentum of the various elements. Several different modes may be distinguished:

(a) Steady state operation at a "neutral temperature", in which heating of foil 102 is offset by cooling of Peltier element 106 and/or thermal conduction to a passive sink.

(b) Rapid raise in temperature, in which the rate of heat increase is determined by the relative values of heating provided by foil 102 and cooling provided by heat transfer to thermal capacity element 104.

(c) Steady state "hot" or "cold", which is generally similar to mode (a), except that the minimum temperature is set by the temperature of element 104 and the maximum temperature is limited by the ability of the foil to provide heat as well as by the temperature of element 104, the higher the element temperature, the higher the probe temperature can be for a given foil. It should be noted that the rate of temperature decrease near the minimum temperatures is sharply reduced. If sufficient power can be pumped into foil 102, the rate of temperature increase is generally not affected by the starting temperature of element 104. Peltier element 106 optionally provides cooling to offset the heating of element 104 by foil 102. Possibly, element 104 is over cooled (e.g., possibly responsive to the foil power) so that when the heating is stopped its average temperature is its desired temperature. This may be used in mode (a) as well. It should be noted that the maximum and/or minimum temperatures selected may also be selected so that they do not cause tissue damage. For example, the maximum temperature being below 70 or 60 degrees Celsius. Alternatively or additionally, a hardware circuit may be provided to limit the heating duration so that it is not too long. This circuit may utilize the temperature probe to determine allowed maximum durations.

(d) Rapid reduction in temperature, in which the rate of decrease is determined by the cooling provided by heat transfer to element 104 and some damping of the rate is available by providing some heating of foil 102.

(e) Varying temperature, which is slower than the rapid changes described above and which may be relatively fast, in which a feedback loop on the foil may be used for controlling the temperature change. Such a feedback loop may also be applied at (a) and (c) and, to some extent in (b) and (d), except that faster sampling may be required. In an exemplary embodiment of the invention, sampling and power control is provided at, for example, 150 times a second. However, slower or faster rates may be used as well.

Referring to FIG. 3B, in an exemplary pulse, the process of determining process parameters is as follows: At 322, a maximum cooling rate is decided on, as is a maximum heating rate. At 324, the lowest desired temperature of the pulse is decided on. At 326, the highest temperature of the pulse is decided on. It should be noted that these decisions are clinical decisions, which then lead to setting of device parameters.

At 328, the maximum temperature allowed for mass 104 is determined. It should be noted that not only the average temperate change rate, but also the shape of the change curve may determine this value. At 330, a foil power setting required to achieve the heating rate is determined. Possibly, no such power setting is available and the user is requested to change his pulse parameters. It should be noted that while well known heat transfer differential equations may be used for these determinations, optionally, a calibration process is used to determine what the values for various cases and interpolation is used for other situations. Alternatively or additionally, a calibration process is used to determine the various parameters of a physical model of the probe, for example, heat transfer rate across mass 104. It should be noted that if probe 104 is over-designed, a real-time feedback system, for example, with temperature sampling at for example 10, 30, 50 or more times per second, can be used for real-time control. Alternatively, a maximum temperature change rate may be aimed for and an actual one recorded. It is expected that in many cases, once the temperature change rate is above a certain value, its exact value does not matter.

In an exemplary embodiment of the invention, the sampling rate is 100 or 150 times a second and each time the actual temperature is compared to a desired temperature (for the desired heating/cooling rate). Based on this comparison, the power to the foil is increased or reduced, if necessary. Possibly, the foil is powered using pulses of power rather than continuous power, and this pulse rate and/or pulse power may be modified. The desired temperature at each time point may be determined for the whole of the change time, at its beginning. Alternatively, new target temperatures are set depending on the actual cooling rate, to compensate so that a total raise/descent time can be achieved.

At 332, element 104 is pre-cooled and a feedback loop is set up to maintain it at this temperature. At 334, foil 102 is heated using a feedback loop to a desired "neutral temperature". A single feedback loop (e.g., a computer program or digital or analog circuit) hardware may be used for both foil 102 and element 104.

At 336, the foil electrification is changed to effect a desired drop or increase in temperature. It should be noted that heat transfer equations are not linear, but are rather differential equations. Thus, if a linear rate is desired over substantially all of the temperature change, non-linear control of the foil is desirable. Alternatively or additionally, some overshoot may be desirable.

In an exemplary embodiment of the invention, calibration of system 200 is performed as follows. An exact temperature sensor is attached to foil 102 in a position that simulates skin contact. Optionally, the sensor is covered with a Kapton tape, to simulate the behavior of the foil sensing elements. Optionally, a thermal sink that emulates human tissue is also used, to include its effect on foil cooling. Steady state temperatures at steps, for example, of 3 degrees Celsius are set and the power to foil 102 modified depending on the exact achieved temperature. Then, various temperature change rates (positive and/or negative) are tried, for example, setting the gain factor of the real-time correction of the foil power based on the results, possibly with different values for different temperature points. The temperature of element 104 is optionally set at 10 degrees Celsius, as the heating foil is generally not limited in power for the required rate changes. Alternatively or additionally, the exact temperature sensor is used to calibrate one or more of the probe temperature sensors. Alternatively or additionally, the response of the probe is used to calibrate a model of the thermal behavior of the probe.

If an array of foil elements is used, each one may be calibrated separately, possibly at different heating conditions of surrounding elements. Alternatively or additionally, the foil elements may be separated by a thermal conducting or non-conducting area.

Figure 4A:
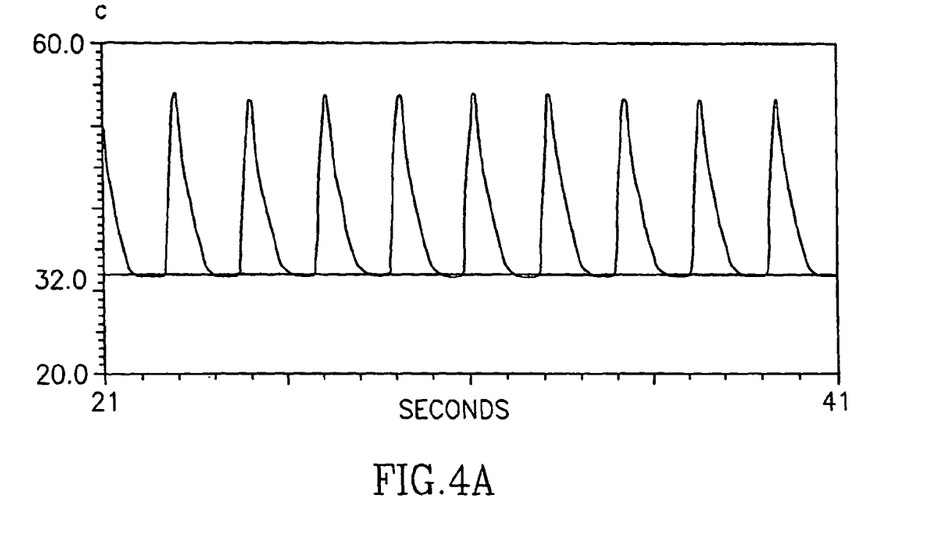
FIGS. 4A-4B show temperature pulses suitable for evoking various nervous effects in accordance with exemplary embodiments of the invention.
Figure 4B:
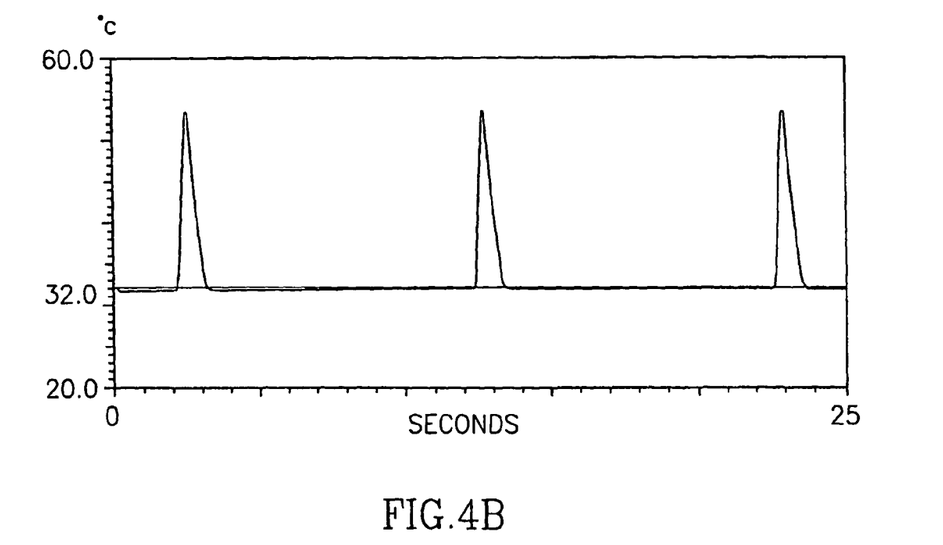

FIGS. 4A-4B show temperature pulses suitable for evoking various nervous effects in accordance with exemplary embodiments of the invention.

FIG. 4A shows a pulse train suitable for selective C-fiber stimulation, by causing a windup effect. In addition, this pulse can also be used to asses a subject's reaction time to second pain, which may serve as an indirect measure of C-fiber conduction velocity. When a series of pain stimuli are given the A-delta fibers are sensitive to only the first pulse, and due to its fast adaptation does not respond to the other pulses. C-fibers do not have this adaptation property, so they will continue and feel the pain stimuli. However C fibers response will be sensed later due to slower conductivity. This situation sometimes create the feeling of a 2nd pain effect. In a diagnostic setting, a test may be done to see if A-delta fibers only respond to the first pain in a set of temporally near pulses and/or if the response of C-fibers to a series of temporally near or somewhat distanced pulses is correct (e.g., relatively uniform in response). It should be noted that after a time the A-delta fiber adaptation disappears, so if the pulses are spaced far enough apart (e.g., another diagnostic parameter) the A-delta fibers should provide a series of responses, reported by the patient and/or measuring system.

Alternatively or additionally, conduction velocity may be measured, for example, by stimulating 2 or more different sites on the leg or hand, via 2 separate but synchronized probes, where the effective nerve distance between them is known, for example, if the two sites are axially displaced on an appendage. Then, calculating for each one the time from stimulation to recording. Then calculating the difference between times in the 2 tests. The velocity is then determined based on the distance between the sites.

In an exemplary embodiment of the invention, such measurements are used for diagnosing pathological effects of diabetes, post-herpetic neuropathy, AIDS, post-chemotherapy and other kinds of peripheral neuropathies. In addition, such measurements may be used for selective assessment of C-fibers, for example for objective evaluation of peripheral nerve system functioning in patients with chronic pain, for example for pain states of unknown etiology (such as fibromyalgia) as well as for the assessment of sensory loss without pain, including "hysterical" sensory loss and/or malingering. In addition, such measurement may also be used for evaluation drug effect in certain neuropathic and pain states. In one example, a same set of test is applied for diagnosis (or a test is applied based on an expected pathology) and addition tests, for example, blood work or previous diagnoses, are used to decide if any pathology is found and/or what its cause might be.

FIG. 4B shows a pulse set suitable for selective stimulation of different sub-groups of A-delta fibers. For example, by controlling the stimulation temperature to be above or below 50 degrees Celsius, high threshold nociceptors (>50 C) and low threshold nociceptors can be distinguished.

An inverse of such pulses may be used to stimulate cold perception (e.g., resting state at a neutral temperature and then a fast plunge to a lower temperature and a fast raise).

As can be appreciated, substantially any shape pulse or pulse train (within the limitations of maximum and minimum temperate and temperature change rates) can be achieved using some embodiments of the invention. Such pulses or trains can be defined using parameters, for example, increase and decrease change rate, duration at non-neutral temperature, rest period, neutral temperature, number of heat/cold pulses in a sequence, frequency of the pulse, minimum temperature during a train, cycle duration, number of trials, delay between trains and pulse train envelope. Various parameters as provided in the TSA system by Medoc Ltd, can also be used. In addition, the system can generate signals, for example TTL level signals for use as triggers or for other uses, for example, signaling events such as stimulus start, reaching temperature destination and stimulus end. Such triggers can be used to synchronize the EEG and the fMRI with the stimulation. Conversely, system 200 may be triggered to start stimulating by an external trigger. In some embodiments of the invention, various audio is generated to a user to indicate a status of the probe. Alternatively or additionally, a visual cue (e.g., LEDs or an LCD display) may be provided on probe 100.

One use of various pulse trains and pulse designs is to distinguish different fibers. Following is a description of various types of fibers, currently known. It should be noted however, that the sensitivity and specificity of some embodiments of the present invention are expected to discover and thereafter selectively stimulate, additional sub-groupings of fiber types. In some cases selective stimulation is achieved indirectly, for example, by using an additional chemical inhibitor or by selectively stimulating twice (or more) different groups of fines, in which only the selectively stimulated fibers are found in both groups. Other ways of distinguishing between fibers may be used as well, using embodiments of the present invention. Exemplary pulse widths are 2 ms, 10 ms, 50 ms, 100 ms and smaller, intermediate or larger lengths. Exemplary pulse attack and decline times are, 2 ms, 10 ms, 50 ms, 100 ms and smaller, intermediate or larger times. Exemplary trains include 2, 4, 10, 40 or a smaller, intermediate or larger number of pulses. Exemplary inter-pulse delays include 2 ms, 10 ms, 40 ms, 100 ms, 300 ms, 1000 ms and smaller, intermediate and greater delays. Exemplary frequencies include 0.1 Hz, 0.5 Hz, 1 Hz, 2 Hz, 4 Hz, 10 Hz, and smaller, intermediate and higher frequencies.

Exemplary temperature changes include 1° C., 3° C., 5° C., 10° C., 20° C., 30° C. and smaller, intermediate or larger temperature changes. Exemplary pulse shapes are symmetric, asymmetric, square, trapezoid, saw-tooth, triangular, linear attach, linear decline, exponential attack and/or exponential decline.

A delta fibers may be divided in to two groups, (a) Type II AMH (A-mechano-heat)—have relatively low heat threshold (<50 C). This type sub serves first pain to heat stimuli. This type is capsaicin sensitive and also can be deactivated using capsaicin. (b) Type I AMH—have high threshold (>50 C); their VRL1 receptor can be activated by intense heat but NOT by capsaicin. This type is insensitive to capsaicin. Type I has a faster conduction velocity than type II. The response to cold is expected to be different for the type I and Type II, for different temperature and/or pulse lengths. In addition, the response is expected to be different from that of C-fibers.

C-fibers may be separated into two groups: (a) Warm fibers, which respond to short-duration heat stimuli at temperatures near the pain threshold in humans (around 45 C). (b) C-meachno-heat fibers, which respond to long-duration stimuli, and stimuli given at higher temperatures.

In an exemplary embodiment of the invention, C-fiber windup is evoked by controlling the stimulation frequency to be fast enough, but not too fast. At the same time, the upper and/or lower temperature are optionally controlled as well. In some cases, it is desirable to control the duration and/or increase or decrease rate. It should be noted that the exact values may vary between people, for different types of fibers and/or for different pathologies. In one example, peak temperature is selected to be lower than that which would activate A-delta fibers (of one or more types).

In some cases, it may be possible to use the synchronization of the stimulation pulse or train with an EEG and/or fMRI system (or other data collection or imaging system) to distinguish the stimulation of certain types of fibers, for example, based on windows (based on expected time of arrival) or based on signal processing (correlation of stimulation train with signal results).

In an exemplary embodiment of the invention, a physiological thermal probe is constructed using the following parts:

Foil 102 is a foil heater manufactured by Minco, USA, for example model AGW20 or 30, cut to size of 24×24 mm, but other sizes and shapes, for example a circle of 30 mm diameter may be used. In particular, foil arrays may be used, for example, a 25 by 25 mm probe based on an array of 100 by 100 individual cells. Such an array may be used, for example, for mapping skin areas, determining relative densities of different fiber types, detecting "blind" areas, and/or for detecting size thresholds for different stimulation types (e.g., integration sizes of fibers) and places. In operation, each array element (one or two dimensional arrays) maybe controlled by itself and/or as part of a group of elements. In some cases, a set of elements may be used to create a particular spatial stimulation pattern and/or profile (e.g., a Gaussian shaped temperature profile as a function of distance from the center of stimulation).

These foil heaters may include two or three embedded Type T thermocouples, with a diameter of 0.13 mm and a response time of 0.04 seconds. Other low capacity heaters may be used instead of foil heaters.

Thermal capacity element 104 may be, for example a plate of aluminum or copper of 2 mm thickness. Increasing its thickness may require a higher power and/or faster response from element 106, do to the increased thermal impedance. The relative heat capacity of the foil and element 104, may be, for example, 1:4, 1:10 or 1:20 or more. The exact values may depend on the design. While the desired thermal impedance may depend on the relative heat capacity and relative temperatures, in an exemplary embodiment of the invention, the thermal impedance is optionally at most 10 times, 3 times, 2 times or less than that of copper of 2 mm thickness. In some designs, what is planned for is the total heat transfer capacity (total and per time unit) of the plate, which includes, its contact area, the conduction of the foil, the plate thickness, its impedance and its thermal capacity.

The sampling rate of the controller can be, for example, every 0.5 seconds, 0.1 seconds or faster, for example, every 6.4 milliseconds.

In some cases, for example for A-delta testing it may be desirable to provide a plurality of stimuli at various locations (e.g., spaced apart by 1, 10, 30, 50 or more mm). However, moving a probe may not be possible in an fMRI setting. In an exemplary embodiment of the invention, an array stimulation probe is used. Alternatively, a plurality of probes that are stimulated in a synchronized (in parallel or series) manner, possibly by a single computer, are used.

Figure 5:
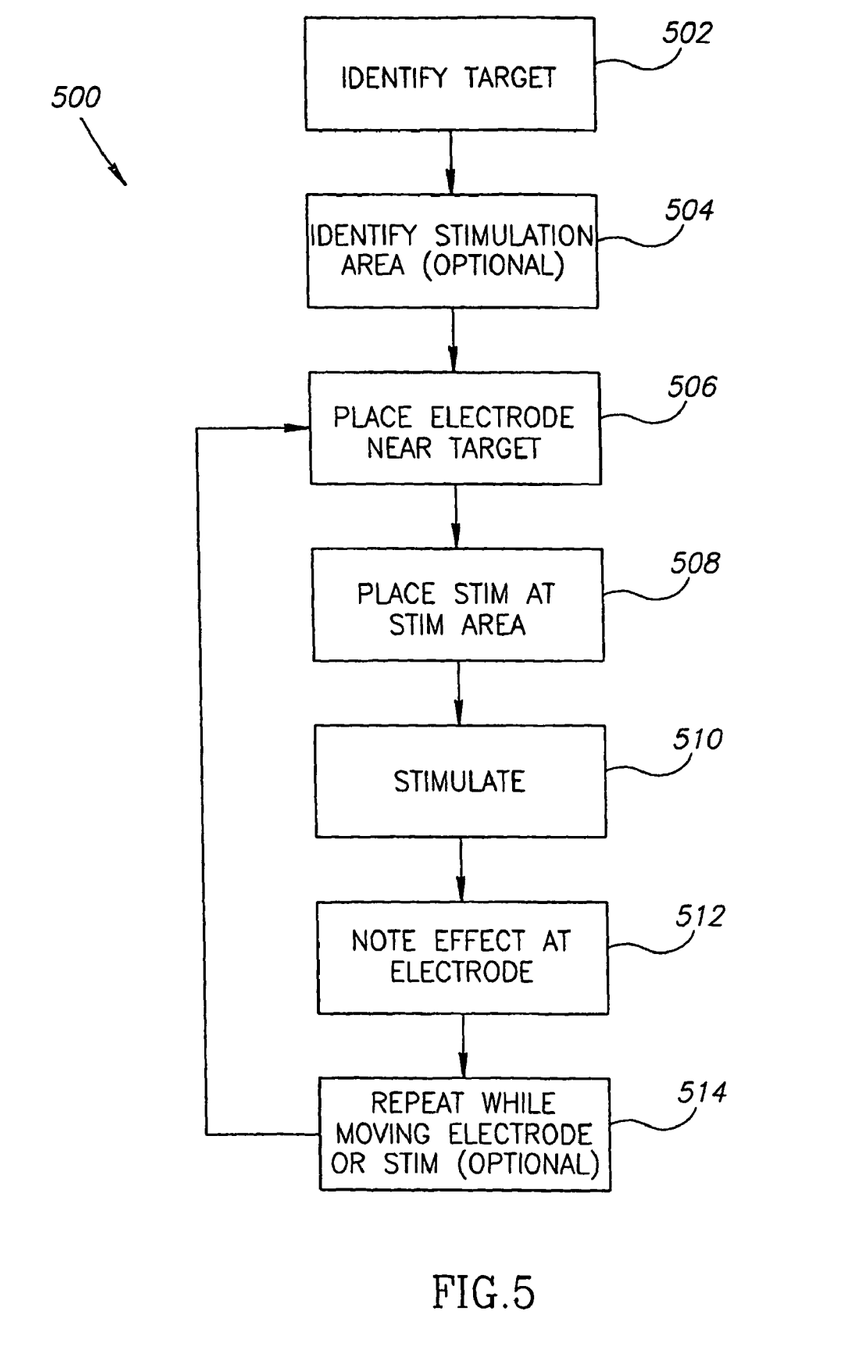
FIG. 5 is a flowchart of a method of brain mapping, in accordance with an exemplary embodiment of the invention.

FIG. 5 is a flowchart 500 of a method of brain mapping, in accordance with an exemplary embodiment of the invention. In this method, a heat/cold stimulation device, for example of the type described above is used to detect a matching between brain areas and sensing from the body. In one example, location of pain areas (optionally of one or more types) in the brain are detected. In another example, location of sensory areas in the brain are detected. Optionally, the areas associated with particular body parts are identified, for example for favoring sensing (after surgery) at the fingers over sensing at the forearms. In some embodiments of the invention, a stimulation device other than described herein may be used, for example, a heating or cooling device using a different principle, a vibration stimulator or an electrical stimulator. Some such devices are provided, for example, by Medoc Ltd. of Ramat Yishai, Israel. An alternative cold causing device is described in "Temporo-spatial analysis of cortical activation by phasic innocuous and noxious cold stimuli—a magnetoencephalographic study", by Christian Maihoffier, et al, in Pain 100 (2002) 281-290, the disclosure of which is incorporated herein by reference. This article also shows a difference between the effect of noxious and innocuous cold spikes and also shows how EVP of such spikes can be detected in the brain, even in a non-invasive manner. An alternative stimulation device selectively couples (e.g., using a linear motor to move the probe against the skin) a pre-cooled or pre-heated probe to tissue for a measured amount of time. Optionally, a neutral temperature probe is then contacted to offset the cooling or heating and/or to mask radiation effects of the probe.

In the exemplary process shown in FIG. 5, a target area for surgery is identified (502), for example, for removal of a tumor or for treatment of an aneurysm. This target area is then accessed, for example, by opening the brain case or using an endoscope (e.g., through the sinuses), or using any other method known in the art.

If the target area is suspected of being adjacent to nerve centers in charge of pain and/or sensory processing, one or more source areas are identified on the body (504), which source areas provide nerve signals processed by the target area nerve centers. In some cases the nerve centers for a particular organ, such as a right hand, will be suspected. In other cases, higher level general nerve centers are suspected and substantially any part of the body (in some cases depending on hemispheric symmetry) may be selected.

The effect of stimulation at the source areas is optionally detected via an evoked potential or other change in electrical activity in the suspected nerve centers adjacent the target area. At 506 one or more electrodes are provided at the target area, for example, on a probe, in an endoscope or catheter, or on a glove of a surgeon.

At 508 (e.g., before after and/or at a same time as 506), a stimulation device, such as device 100 is placed at a source location. In some embodiments, a plurality of stimulation devices are placed at one or more source areas and optionally activated together or in series.

At 510, the stimulation device(s) are activated, for example to create a heat spike or a cold spike with a minimum temperature of between −10 and +5 degrees Celsius. Other temperatures may be used as well. For example a minimum temperature or 8 degrees or of 10 degrees.

At 512, the effect of the stimulation is noted at the electrode. In one example, a map of the sensitive brain centers is determined using the electrode and/or the stimulation device. In another embodiment, important brain areas are marked, for example on an image guided surgery system or on the brain itself. Alternatively or additionally, the tissue which may be removed without damage to pain sensing, is marked At 514, some or more of the steps of the process are repeated, for example while moving the electrode and/or stimulation device to a new location.

Alternatively or additionally, to use during brain surgery, such stimulating and checking for nervous response may be used during other types of surgery, for example, during reattachment of amputated limbs (in which case EEG sensing may be sufficient), or for procedure son the spinal column.

Figure 6:
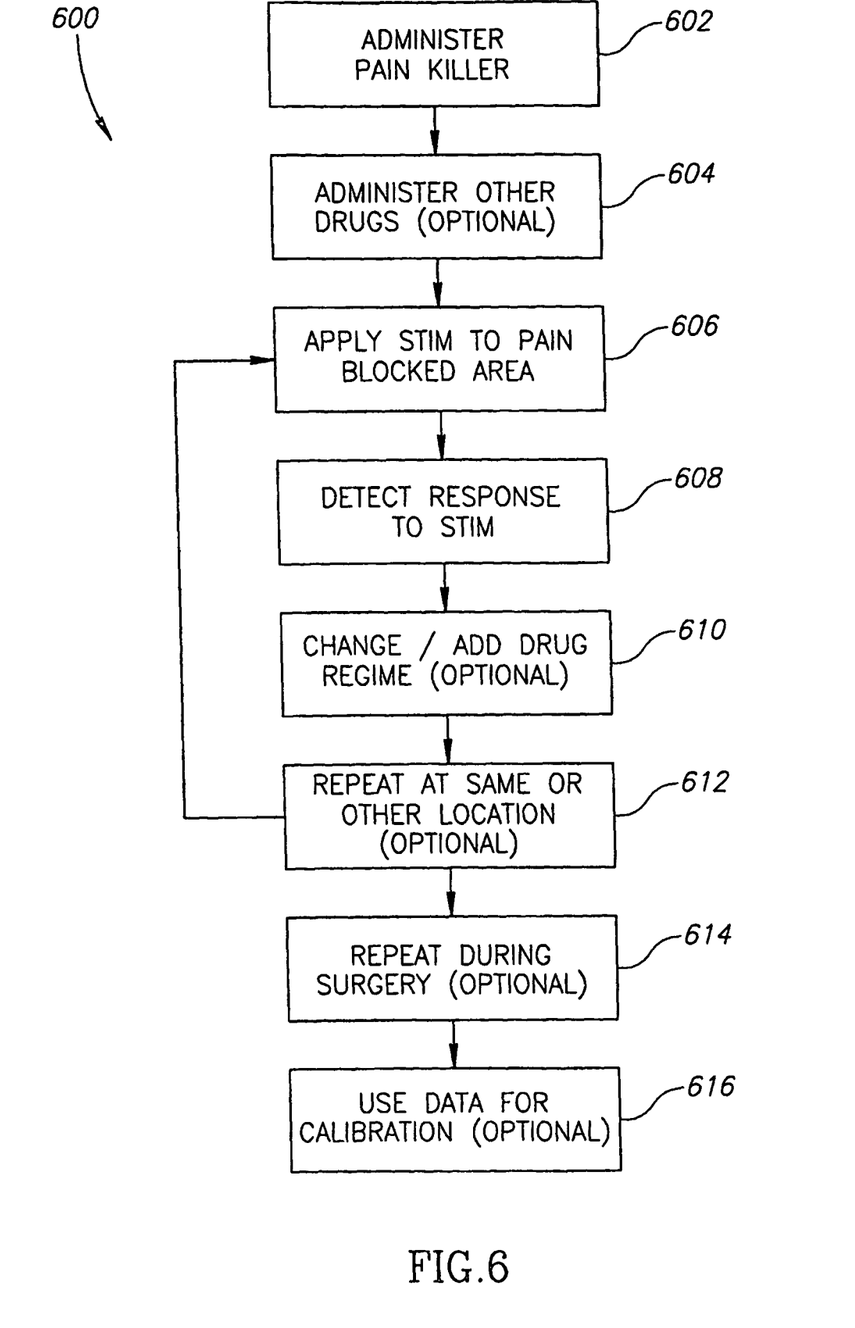
FIG. 6 is a flowchart of a method of monitoring during surgery, in accordance with an exemplary embodiment of the invention

FIG. 6 is a flowchart 600 of a method of monitoring during surgery, in accordance with an exemplary embodiment of the invention. During surgery, patients are provided with a combination of drugs intended to have three effects: loss of consciousness, pain prevention and immobility. Failure of the pain prevention or failure of the loss of consciousness is difficult to determine today. Possibly, this results in over medication, in order to reduce the other possible effects, of lingering pain and of memories of the surgery.

At 602, a pain killer drug (or a mixture thereof), for example an analgesic agent, and anesthetic agent or narcotic agent is administered to a patient. Other pain preventing methods, such as electric fields and hypnosis may be used as well. Optionally, the amount of material administered is dependent on calibration results for a range of patients and/or for this patient, generated for example as will be described below.

At 604, optionally, additional drugs are administered. These drugs may be administered, for example, at the same time, before and/or after the pain killer is administered.

At 606, stimulation is applied to a location on the body where from which pain is supposed to be blocked. Optionally, stimulation is also applied before a partial or a complete pain blocking effect is expected. This may be used, for example to determine a base-line sensitivity of the patient or to determine a temporal profile of the effect of the drug.

At 608, a response in the brain to the stimulation is detected. Possibly, no response is detected, for example 1*f* sufficient pain killer drug is administered. Such detection may be provided, for example, using EEG measurement, optionally integrated into a device for tracking patient consciousness level, for example a Bispectral Index (BIS)® Techology provided by Aspect Medical Systems.

At 610, drug dosage and/or administration profile and/or type are optionally changed in response to a detection or lack thereof and/or a change in one or more characteristics of the detected signals. As noted herein, a calibration session may be used to match different measured patterns with different drugs effects.

At 612, stimulation is optionally repeated at multiple times and/or body locations. Optionally, locations are changed to prevent or avoid local adaptation of the nerve endings to stimulation.

Optionally, 614, stimulation and detecting is repeated during surgery, to serve as a monitoring process and/or to drive manual and/or automatic feedback loops of changing of drug administration. Optionally, the detection system controls the level of administration and/or other characteristics thereof in response to a pre-set program that takes the patient response to pain stimulation into account.

Optionally, the process described above is used during surgery. Alternatively or additionally, (616) it is applied before surgery, for example to assess the sensitivity to pain and/or rate of metabolization and/or effect in the patient of a particular drug or drug mixture. Optionally, a multiplicity of such measurements are used to determine properties of a drug for a large group of people, possibly by repeating applying and sampling the effect for a statistically meaningful number and/or selected categories of people. Optionally different values are collected for different ages, weights, genders, races and/or other biologically meaningful parameters, such as liver function.

Alternatively or additionally to tracking the effect of pain killers, the effects of consciousness removers and/or a level of consciousness may be determined. In an exemplary embodiment of the invention, non-pain stimulation, such as vibration, or other stimulation, such as electric current, is used to provoke a brain response. It is expected that the response be correlated, at least to some degree with a level of consciousness. Optionally, a calibration for a patient is determined. Optionally, also the measurements taken in FIG. 6 are calibrated for a level of consciousness, as it is possible that in at least some patients pain may be reduced or increased depending on level of consciousness. Various prior art methods of measuring level of consciousness are known. Optionally, the level of consciousness detected using such methods is corrected by a measure of the change in pain perception.

Alternatively or additionally, pain detection is used to assess the effect of a pain killer applied not during surgery, for example for regular patients or for chronic pain patients. Optionally, such a patient determines a base-line of pain which is acceptable when applied by a device as described above or other pain causing device. When a pain killer is administered, the patient (or other person or a computer) sets the administration profile so that the effect on a known pain stimulation is of a known amount. Possibly, this allows a patient to feel control over the degree of pain and/or the degree of pain blocking. Optionally, real-time monitoring is provided, for example by applying a heat or cold pulse and assessing a patient estimation of the pain level (which can be translated into a current sensitivity to pain, if previous measurements have been acquired). Patient input may be, for example, manual or automatic.

It should be noted that spatial effect of a pain killer (e.g., a locally applied or a systemically applied pain killer) may also be assessed.

Optionally, a stimulation device is used to assess the efficacy of a pain killer used in surgery. In one example, the method described above is used to determine if a pain killer has achieved a desired effect. For example, such a device may be used in dentistry to assess when a patient is ready for treatment after injection of a pain killer. Periodic or continuous assessment may be provided as well. It should be noted that the stimulation may be applied to the treatment location, or to a different location controlled by the same nerve.

Optionally, circuitry for generating an alert of certain ranges are exceeded, is provided. For example, such circuitry can generate an alert if a consciousness level goes too high or too low or if a pain sensing level goes too high or too low.

It will be appreciated that the above described methods and apparatus may be varied in many ways, including, changing the order of steps, and/or performing a plurality of steps concurrently. It should also be appreciated that the above description of methods and apparatus are to be interpreted as including apparatus for carrying out the methods and methods of using the apparatus. Specifically, it is noted that substantially all the methods of the present invention may be performed automatically by a processor without human intervention. Also within the scope of the invention is software suitable for carrying out the methods of the invention or parts thereof, stored on a computer readable media and/or installed on or in combination with suitable hardware, such as a computer.

The present invention has been described using non-limiting detailed descriptions of embodiments thereof that are provided by way of example and are not intended to limit the scope of the invention. It should be understood that features and/or steps described with respect to one embodiment may be used with other embodiments and that not all embodiments of the invention have all of the features and/or steps shown in a particular figure or described with respect to one of the embodiments. Variations of embodiments described will occur to persons of the art. For example, non-foil heaters may be used. In addition, while separate elements are shown, they may be combined, for example, a monolithic transparent heat conducting element (e.g., a diamond) may be used as both element 104 and heating foil 102, with heating provided using back illumination of a surface of the monolithic element. Other types of heaters, with low thermal capacity may be used as well. The probe is optionally provided with a disposable sheath and/or is made of a sterilizable material.

It is noted that some of the above described embodiments may describe the best mode contemplated by the inventors and therefore may include structure, acts or details of structures and acts that may not be essential to the invention and which are described as examples. Structure and acts described herein are replaceable by equivalents which perform the same function, even if the structure or acts are different, as known in the art. Therefore, the scope of the invention is limited only by the limitations used in the claims. When used in the following claims, the terms "comprise", "include", "have" and their conjugates mean "including but not limited to".

The invention claimed is:

1. A method of controlling the application temperature of a probe, comprising:

providing a thermal capacity element with a relatively large thermal mass at a first temperature, providing a heat control element including a part having a relatively small thermal mass, and where said heat control element is electrically controlled and where said relatively small thermal mass is in thermal contact with said large thermal mass and where said small thermal mass is adapted to apply an application temperature to a body part in contact therewith, said small thermal mass having a thermal mass less than one quarter the thermal mass of said large thermal mass; and controlling the application temperature by controlling the heat control element in a manner which generates an application temperature of said small thermal mass other than said first temperature, said controlling the application temperature comprising offsetting a thermal effect of the large thermal mass on said application temperature by said controlling said heat control element of said small thermal mass.

2. A method according to claim 1, comprising stopping said heat control element to produce a sharp change in temperature of said small thermal mass.

3. A method according to claim 1, comprising powering said heat control element to produce a sharp change in temperature of said small thermal mass.

4. A method according to claim 1, wherein said providing said small thermal mass comprises providing said small thermal mass at a temperature different than said first temperature.

5. A method according to claim 1, wherein said thermal masses have a ratio of over 1:50.

6. A method according to claim 1, wherein said thermal masses have a ratio of over 1:100.

7. A method according to claim 1, wherein said thermal masses have a ratio of over 1:1000.

8. A method according to claim 1, wherein controlling comprises generating at least one sharp temperature spike of at least 10° C. including a sharp leading edge, a duration of less than 2 seconds and a sharp trailing edge.

9. A method according to claim 1, wherein controlling comprises controlling in a manner which generates a temperature spike with substantially linear-rate temperature changes.

* * * * *